United States Patent [19]

Gjessing

[11] 4,047,715
[45] Sept. 13, 1977

[54] FRICTION TYPE ERGOMETER APPARATUS

[76] Inventor: Einar Tandberg Gjessing, Hans Nielsen Hauges vei 22 F, 1500 Moss, Norway

[21] Appl. No.: 584,503

[22] Filed: June 6, 1975

[30] Foreign Application Priority Data

June 7, 1974 Norway .................................. 742081

[51] Int. Cl.² ............................................. A63B 21/00
[52] U.S. Cl. ............................... 272/132; 272/DIG. 4; 272/72
[58] Field of Search ........ 272/79 D, DIG. 3, DIG. 6, 272/81, 131–134, 72, 67, 71, 73

[56] References Cited

U.S. PATENT DOCUMENTS 1,258,469   3/1918   Ruden ..................................... 272/81
3,572,700   3/1971   Mastropaolo ....................... 272/79 R
3,822,599   7/1974   Brentham ....................... 272/79 R X

FOREIGN PATENT DOCUMENTS 1,078,777   8/1967   United Kingdom ................. 272/131

Primary Examiner—Richard C. Pinkham
Assistant Examiner—William R. Browne
Attorney, Agent, or Firm—Watson, Cole, Grindle & Watson

[57] ABSTRACT

An ergometer rowing apparatus having a friction brake system. The rowing apparatus also includes a varying diameter worm pulley providing a variable speed pattern of the pulley in accord with the desired speed pattern set by the user. A free wheel gear permits rotational movement of a fly wheel in only one direction during movement of a user in only one direction when acting upon the apparatus.

6 Claims, 7 Drawing Figures

FRICTION TYPE ERGOMETER APPARATUS

BACKGROUND OF THE INVENTION

The present invention relates to an ergometer apparatus, such as an ergometer bicycle or an ergometer rowing apparatus, comprising a flywheel, means actuated by muscle power for driving the flywheel, and a brake device for the flywheel comprising a stationary brake string frictionally engaging a peripheral surface rotating with the flywheel.

In addition to a training of the person using an ergometer apparatus, such apparatus is used to obtain an accurate measurement of the work performed. The work is proportional to the number of revolutions of the flywheel and the frictional force braking the flywheel. The number of revolutions of the flywheel is easily measured, whereas the frictional force is difficult to measure and is above all difficult to maintain constant in operation of the apparatus. In ergometer bicycles there is often used a nylon string which encircles the flywheel and which is tightened in order to obtain the desired frictional force. The frictional force depends on the coefficient of friction and the tightening force, both of which vary with the temperature and are therefore influenced by the generated frictional heat. A certain frictional force set before the apparatus is put into operation will therefore usually change during operation.

According to a previous suggestion (which is believed not to be published prior to the priority date of the present invention) the end of the string which would be the rear end if the string had moved with the rotating peripheral surface, may be loaded by a certain force S, and the string may be wound so many times around the peripheral surface that the necessary load $s$ in the opposite end of the string may be disregarded, whereby the frictional force F may be assumed to be approximately equal to S. However, experience shows that it is not possible to reduce the load $s$ on the forward end of the string to such a negligible value, since a variation in the coefficient of friction may cause the rotating peripheral surface to carry with it the brake string. In practical embodiments the force $s$ has therefore been of the magnitude of 7 to 8 per cent of S, which is much too large for this force to be ignored if a satisfactory accuracy is to be achieved. It has also been suggested that the error in the work measurement introduced by the ignorance of $s$ may correspond to the frictional losses in the transmission, but this is a presumption which is much too rough to be satisfactory in accurate work measurements.

SUMMARY OF THE INVENTION

The present invention especially aims at providing an ergometer apparatus in which the force transmission from the person using the apparatus to the flywheel may be adapted to various working activities, and in which the measuring of the work performed may be carried out in a very simple and easy manner, the frictional force being maintained substantially constant. At the same time the apparatus should be so simple and sturdy as not to require much maintenance and not to be dependent upon narrow tolerances.

The invention will be explained with reference to a rowing apparatus, but the principles on which the rowing apparatus illustrated is based may also be used in other training apparatuses.

The apparatus according to the invention is first of all characterized by means permitting the force S loading the end of the brake string which would be the rear end if the string had moved with said peripheral surface, to be varied in accordance with the variations in the force $s$ loading the opposite or forward end of the string, said force S being composed of a constant force corresponding to the desired frictional force F plus an additional force corresponding to the force $s$, whereby the difference between the forces at the two ends of the string may be kept approximately constant by adjusting the additional force in accordance with the value of $s$.

The force $s$ may be indicated visually and the additional force in the rear end of the string adjusted accordingly. It is, however, not necessary to indicate $s$ in ounces, grams or other established units since the value of $s$ is not to be used in any calculations. The unit in which the force is indicated is therefore of no concern, provided it permits a compensation of $s$ by a corresponding additional loading of the rear end of the string. The unit in which $s$ is indicated may for instance be the weight of certain loading elements. However, it is not necessary to indicate the value of $s$ so as to be readable by a person who may then adjust said addition force. The compensation of $s$ may also be effected in an automatic manner which requires no reading of $s$ and which is thus not dependent on human attention.

As will be understood, the invention uses the same known brake principle for drums as the previous suggestion referred to above. However, according to the invention the force $s$ is compensated in such a manner that a constant frictional force is obtained with great accuracy.

According to another feature of the invention in which the driving means for the flywheel comprise a handle movable in a path simulating the activity the energy of which is to be measured, and a taut wire means secured to the handle and wound around a pulley connected to the flywheel, the pulley has a groove which extends in several adjacent windings around the pulley, the distance of said groove from the rotational axis of the pulley varying continuously according to a desired pattern, so that a movement of the handle according to a desired speed pattern corresponds to an approximately uniform rotational movement of the flywheel.

Further objects, features and advantages of the invention will appear from the subsequent description of a rowing apparatus according to the invention.

DETAILED DESCRIPTION OF THE PREFERRED EMBODIMENT

Figure 1:
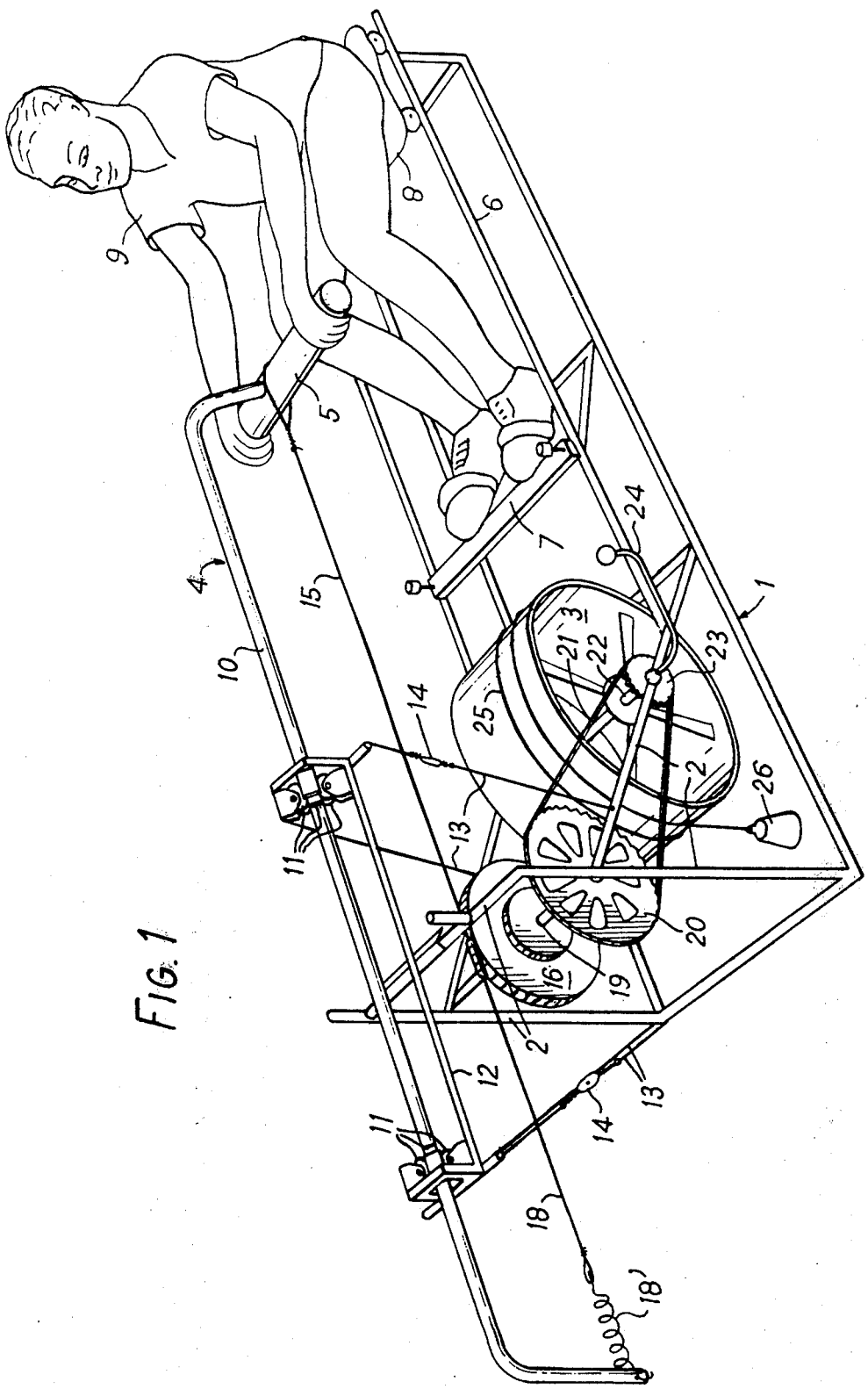
FIG. 1 is a perspective view of an apparatus according to the invention.

The rowing apparatus illustrated comprises a frame 1 which may rest on the floor or the ground, and which at one end carries a rack 2 for a drum-shaped flywheel 3, an actuating means 4 having a handle 5, and means which through a flywheel gear couple the actuating means 4 to the flywheel 3 for rotation thereof. Over the rest of its length the frame 1 carries rails 6 for a slide 8. Between the rails 6 there is also attached an adjustable footboard 7 so that the person 9 using the rowing apparatus may pull the handle 5 in a manner similar to that of the oar in a racing rowboat and return the handle towards the drum 3 for another "stroke."

Figure 7:
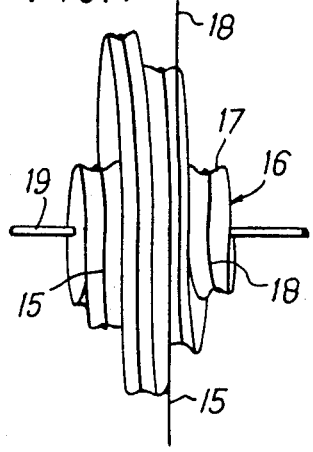
FIG. 7 illustrates the pulley which according to the invention is used for transforming the desired speed of the working movement to an approximately uniform speed of the flywheel.

The actuating means 4 comprises a rod 10 which is mounted for longitudinal displacement in roller guides 11 in a cradle 12 which in turn is tiltably mounted at the upper end of the rack 2. The tilting movement may be restricted by means of guy ropes 13 between the cradle 12 and the frame 1 or the rack 2. The length of the guy ropes 13 may be adjusted by means of wire stretchers 14. Thereby, it becomes possible to tip the handle down at the end of the "stroke" in a similar way as in a racing boat, whereas the stroke itself is carried out substantially horizontally at a level corresponding to that of the oar handle when the oar blade is submerged. To the handle 5 there is connected a wire, string or the like 15 which extends to a pulley 16 having a groove 17 extending in several adjacent windings around the periphery of the pulley 16, the distance of said groove from the rotational axis of the pulley varying continuously as shown in FIG. 7. Since the groove 17 extends in a spiral or worm configuration the pulley 16 will be referred to as a worm pulley. As illustrated in claim 6 a wire 15 extends along the groove 17 in one direction to one end of the worm pulley, at which end the wire is secured. A second similar wire or string 18 is secured to the other end of the worm pulley 16 and extends along the groove to the point where the wire 15 enters the worm pulley. At this point the wire 18 leaves the worm pulley in a direction opposite of that of the wire 15. The opposite end of the wire 18 is connected through a tensioning spring 18' to the end of the rod 10 opposite the handle 5. The wires connecting the rod 10 and the worm pulley make the latter rotate when the rod 10 is displaced. The wires 15 and 18 and the groove 17 in the pulley 16 may, of course, also be replaced by other equivalent coupling means between the handle 5 and the worm pulley 16. For instance, the rod 10 may be provided with teeth for engagement with a spiral teeth rack on the pulley 16. The worm pulley 16 is mounted on a shaft 19 which is mounted in the rack 2. The worm pulley 16 as well as a sprocket wheel 20 are secured to the shaft 19 for rotation therewith. A chain 21 transmits the rotational movement of the sprocket wheel 20 to a smaller sprocket wheel 23 which through a free wheel gear, which will not be described in detail, for instance a free wheel gear of the type used in bicycles, drives a shaft 22 to which the drum or the flywheel 3 is secured so as to rotate with the shaft. If desired, the free wheel gear may also have an adjustable gear ratio or include a gear which may be shifted by means of a lever 24.

Figure 6:
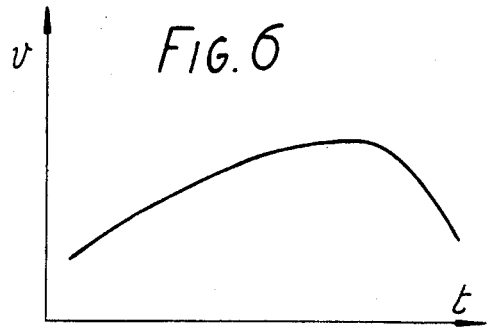
FIG. 6 illustrates a curve indicating the desired speed of the rowing motion versus the time.

When the "oarsman" pulls the handle 5, the drum or flywheel 3 will consequently be rotated. The free wheel gear ensures that the handle may be moved in the opposite direction without influencing the rotation of the flywheel. The varying distance of the groove 17 in the worm pulley 16 from the rotational axis of the pulley is such that the desired speed or rythmic movement of the handle 5 will be transformed to an approximately constant rotational speed of the worm pulley. As an example, FIG. 6 illustrates the desired speed of the handle 5 during the stroke in a certain boat. For the oarsman 9 to be able to transfer energy to the flywheel 3 in the middle phase of the stroke, he must follow the speed curve on which the shape of the worm pulley 16 is based. Thereby, the work performed in the rowing apparatus will indicate the work which the oarsman can perform in a boat in which this speed distribution or rythm is present. This permits selection of oarsmen fitting special boats and above all selection of the best stand-by for a certain crew having an established technique and rythm. Thus, in the rowing apparatus the performance of each candidate may be tested independently of the work of the other oarsmen, and still the candidate may be subjected to the rowing style of the crew. The gear, which may be adjustable in operation, permits stepwise adjustment of the resistance of the apparatus in order to simulate for instance easy rowing, uniform rowing over a racing stretch, spurting and/or rowing against the wind.

Figure 2:
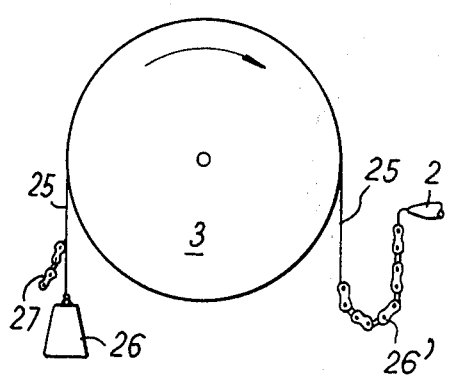
FIGS. 2 and 3 are a side view and a plan view, respectively, of the flywheel in the apparatus including the brake string wrapped around the flywheel and means for exerting a loading force in both ends of the string.
Figure 3:
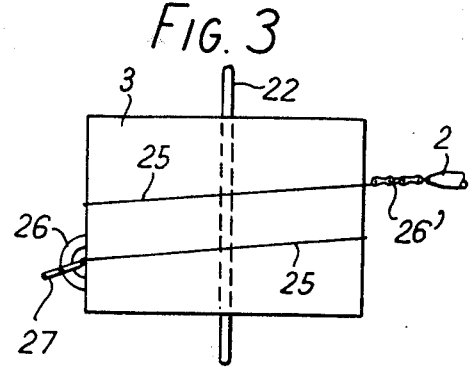

The resistance of the rowing apparatus or the work performed in carrying out a stroke in a certain time can also be changed by varying the braking force on the drum 3. This is easily possible with the chosen brake system which consists of a string 25 which is wrapped around the cylindrical peripheral surface of the flywheel drum 3, and which is loaded by a weight 26 of for instance 5 kg at one end, viz. the end which would be the rear end if the string were rotating with the drum 3. This end will subsequently be called simply the rear end, whereas the opposite end of the string will be called the forward end. The weight 26 exerts on the string a force which will be designated by S. The force $s$ required in the forward end of the string in order together with the frictional force F to balance the force S is determined by the following equation:

$$S = s \cdot e^{\mu a}$$

in which $\mu$ is the coefficient of friction and $a$ is the arc of contact. Accordingly, the frictional force F is $S - s$. Assuming a coefficient of friction of 0.3 and 1½ full windings of the string as shown in FIGS. 2 and 3, $S = 16.90 \cdot s$. Thus, if S in a certain case is 50 N, $s$ must be about 2.96 N. $s$ may for instance be indicated by a spring balance, a pendent balance or the like, the forward end of the string being secured to the rack 2 or the like through the balance. If S is increased to $S' = 50 + s = 52.96$ N, $s'$ will become 3.12 N and the $S - s$ will be 49.84 N, i.e. very close to 50 N. However, a suitable load in the forward end may also be provided by replacing the balance with a heavy, flexible element, such as a link chain 26', suspended in U-form. If the weight of the chain links acting on the string 25 is too small to provide the required force $s$ in the string, the weight 26 will pull the string in a direction opposite the direction of rotation of the drum, whereby an increasing number of chain links will act on the string 25 until the required string force $s$ has been achieved. Accordingly, the number of chain links between the string and the lowermost point of the U is an indication of the force $s$. In order to achieve a predetermined frictional force, the force S is increased by loading the rear end of the string with smaller elements 27 in addition to the weight 26, the weight of these smaller elements together corresponding to the weight of the chain links of the chain 26' acting on the string 25. For instance, the elements 27 may consist of chain links similar to those used in the chain 26'.

Figure 4:
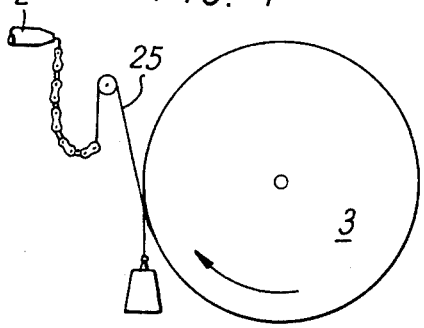
FIG. 4 illustrates an alternative arrangement of the string.

In FIG. 4 an embodiment is illustrated which in principle does not deviate from the embodiment in FIGS. 2 and 3, but in which the string is wrapped a full number of revolutions, for instance twice, around the drum 3.

Figure 5:
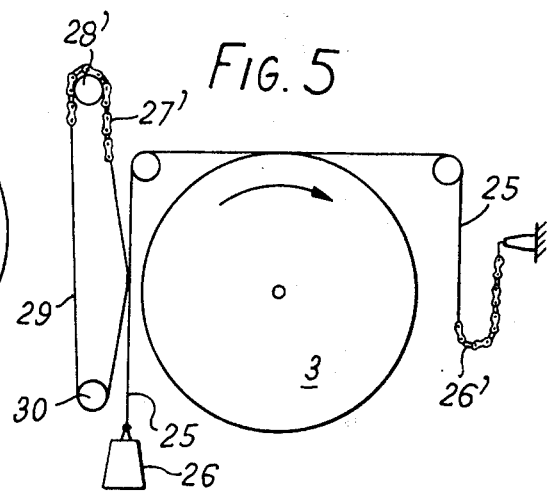
FIG. 5 illustrates an arrangement permitting automatic compensation of the force $s$ in the forward end of the string.

In FIG. 5 there is diagrammatically illustrated how the additional load in the rear end of the string can be varied automatically in accordance with the force $s$ or the length of the flexible element or link chain 26' loading the forward end of the string. In this embodiment the rear end of the string is secured to a similar heavy, flexible element in the form of a link chain 27' which passes over a roller 28 and is connected into a loop by a lighter, flexible element 29 guided over a roller 30. When the load in the forward end is increased due to movement of the string 25, more of the chain 27' is pulled over the roller 28, thus biasing the loop and loading the rear end of the string 25. By an appropriate choice of the weight of the chain 27' per unit length the increase of the load in the rear end of the string can be kept equal to the increase to the force $s$ provided by the link chain 26'.

What I claim is:

1. An ergometer apparatus comprising:
   a flywheel;
   means operatively connected to said flywheel for rotating said flywheel in one direction, said means being actuated by muscle power;
   a peripheral surface operatively associated with said flywheel for simultaneous rotation therewith; and,
   brake means for braking the rotation of said flywheel while a user is applying a force in order to resist rotation of said flywheel, said brake means including: a substantially stationary brake string extending in the peripheral direction of said peripheral surface and in frictional engagement therewith; means for providing in the rear end of said brake string, with regard to the direction of rotation of said peripheral surface, a load force S that is sufficiently large to prevent the string from rotating with the peripheral surface; and means for automatically providing a varying load force $s$ on the forward end of said string in response to changes in coefficient of friction of said peripheral surface, said force $s$ equals the value $S \cdot e^{-\mu \alpha}$ where $\mu$ is the coefficient of friction between the peripheral surface and the string and $\alpha$ is the arc of contact therebetween, so that the rotation of said peripheral surface is braked by a frictional braking force $F = S - s$ where $F$ has a substantially constant value, during a user's exertion on said means operatively connected to said flywheel, regardless of any variance in the coefficient of friction.

2. An apparatus according to claim 1, wherein said means for providing said force $s$ to said forward end of said brake string provides such force in such a manner as to permit reading of said loading force $s$.

3. An apparatus according to claim 1, wherein said force $s$ acting on said forward end of the brake string is provided by a heavy, flexible element suspended in a U-form, one end of said flexible element being secured to said string and the other end to a rigid member of the apparatus, whereby the length of said flexible element between said string and the lowermost point of the U will provide a measurement of said force $s$ and thereby an indication of the additional force to be exerted on said rear end of said string.

4. Ergometer apparatus comprising:
   a flywheel;
   a reciprocating actuating means reciprocated by muscle power of a user in a forward direction and a return direction;
   a force transmission means operatively coupling said actuating means during movement in its forward direction, the direction in which the flywheel rotates, to said flywheel for rotating said flywheel only in the forward direction; and
   brake means for applying a constant braking force to the rotation of said flywheel;
   said transmission means including a rotatable wheel coupled to said flywheel by a free wheel gear, said rotatable wheel having a peripheral engagement surface in engagement with said actuating means, said peripheral engagement surface extending in several adjacent turns, said turns successively receiving the actuating means during reciprocation of said reciprocating actuating means, said turns being arranged at varying radial distances from the rotational axis of said rotatable wheel, such distances being selected in accordance with a desired speed pattern, representative of a series of desired speeds, for each forward stroke of said reciprocating actuating means so that when said actuating means is moved in accordance with such desired speed pattern then said rotatable wheel rotates with an approximately uniform rotational movement, and said free wheel gear permitting movement of said actuating means in its return direction without affecting the rotation of said flywheel.

5. An apparatus according to claim 4, wherein: said rotatable wheel is a pulley; said engagement surface is a grooved surface; said reciprocating actuating means includes an elongated handle rod extending transversely to the rotational axis of said pulley on both sides thereof; and further comprising coupling means engaging said grooved surface and including a first wire extending from one end of said handle rod to a position in said grooved surface intermediate the ends thereof and following said grooved surface to one end where said first wire is secured to said pulley, and a second wire extending from the other end of said handle rod to said intermediate position and following said grooved surface to the other end of said grooved surface where said second wire is secured to said pulley.

6. An apparatus according to claim 5, wherein said transmission means includes a gear having a stepwise or continuously adjustable gear ratio, said gear being provided between and connecting said pulley and said flywheel.

* * * * *